United States Patent
Kleen et al.

(10) Patent No.: US 7,408,648 B2
(45) Date of Patent: Aug. 5, 2008

(54) METHOD FOR TOMOGRAPHICALLY DISPLAYING A CAVITY BY OPTICAL COHERENCE TOMOGRAPHY (OCT) AND AN OCT DEVICE FOR CARRYING OUT THE METHOD

(75) Inventors: Martin Kleen, Furth (DE); Marcus Pfister, Bubenreuth (DE); Thomas Redel, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 146 days.

(21) Appl. No.: 11/429,176

(22) Filed: May 5, 2006

(65) Prior Publication Data
US 2006/0264743 A1    Nov. 23, 2006

(30) Foreign Application Priority Data
May 6, 2005 (DE) .................... 10 2005 021 061

(51) Int. Cl.
*G01B 9/02* (2006.01)
*G01B 11/02* (2006.01)

(52) U.S. Cl. ........................ 356/479; 356/497

(58) Field of Classification Search ............... 356/477, 356/479, 497, 498; 250/227.19, 227.27; 600/425, 431
See application file for complete search history.

(56) References Cited

U.S. PATENT DOCUMENTS

| | | | |
|---|---|---|---|
| 6,134,003 A * | 10/2000 | Tearney et al. | 356/479 |
| 6,735,463 B2 * | 5/2004 | Izatt et al. | 600/476 |
| 7,072,046 B2 * | 7/2006 | Xie et al. | 356/479 |
| 7,187,450 B2 * | 3/2007 | Drabarek | 356/497 |
| 2003/0103212 A1 | 6/2003 | Westphal et al. | |
| 2007/0076213 A1 * | 4/2007 | Kato | 356/479 |

FOREIGN PATENT DOCUMENTS
WO    WO 97/32182 A1    9/1997

* cited by examiner

*Primary Examiner*—Michael A Lyons

(57) ABSTRACT

The invention relates to a method for tomographically displaying a cavity by optical coherence tomography (OCT) and to an OCT device, wherein the path length of a measuring light beam in the catheter can change as a result of a movement of the catheter and brings about a change in the display scale, wherein a possible change in the path length of the measuring light beam in the event of a movement of the catheter is electronically determined and automatically compensated.

13 Claims, 4 Drawing Sheets

METHOD FOR TOMOGRAPHICALLY DISPLAYING A CAVITY BY OPTICAL COHERENCE TOMOGRAPHY (OCT) AND AN OCT DEVICE FOR CARRYING OUT THE METHOD

CROSS REFERENCE TO RELATED APPLICATIONS

This application claims priority of German application No. 102005021061.9 filed May 6, 2005, which is incorporated by reference herein in its entirety.

FIELD OF THE INVENTION

The invention relates to a method for tomographically displaying a cavity, preferably a blood vessel, by Optical Coherence Tomography (OCT), in that a scanning head with a catheter is inserted into the cavity to be optically scanned and the surroundings of the scanning head are displayed in a tomographical display on the basis of detected interferences and their intensities between a measuring light beam and reference light beam, wherein the path length of the measuring light beam in the catheter can change as a result of a movement of the catheter and brings about a change in the display scale.

The invention also relates to an OCT (=Optical Coherence Tomography) device for tomographically displaying an examined object, comprising a coherent laser light source, a splitter for splitting the light emitted by the laser light source, a length-adjustable reference light path into which the laser light source irradiates with a first portion of the emitted light (=reference light beam), a length-adjustable measuring light path in a catheter, into which the laser light source irradiates with a second portion of the emitted light (=measuring beam), comprising an optical scanning head which radially scans its surroundings at least in one plane, an interference detector with an input for the reference light path and the measuring light path, and a computing and display device for tomographically displaying the surroundings of the scanning head on the basis of the detected interference intensity between measuring beam and reference beam, wherein a part of the OCT device is visible in the tomographical display.

BACKGROUND OF THE INVENTION

The basic principle of OCT is based on white light interferometry. This method compares the propagation time of a signal using an interferometer, usually a Michelson interferometer. In this case an optical path with known optical wavelength, the reference path of the interferometer, is used as the reference for the measuring path. The interference of the signals from both paths produces a pattern, as a result of optical cross correlation, from which pattern the relative optical wavelength—an individual depth signal—can be read. In the one-dimensional grid method the beam is transversely guided in one or two directions, whereby a two-dimensional scan or a three-dimensional tomogram may be taken. The outstanding property of the OCT lies in the decoupling of the transversal resolution from the longitudinal resolution. In contrast thereto both the axial resolution—depth-wise—and the transversal—lateral—resolution depend on the focusing of the light beam in conventional light-optical microscopy.

The fields of application are primarily in medicine, in particular in ophthalmology, and in early cancer diagnosis, for skin examination or in the field of examination of vessels which is considered in particular here. Reflections on boundaries of materials with different refractive indices (membranes, cellular layers, organ boundaries) are measured in this case and thus a two- or three-dimensional image is reconstructed.

The use of OCT is limited by the penetration depth of electromagnetic radiation into the object being examined and by the bandwidth. Since 1996 sophisticated broadband [lasers] have enabled the development of UHR-OCT (Ultra High Resolution OCT) which has advanced the resolution from a few tens of micrometers ($\mu m$) to fractions of micrometers. Subcellular structures in human cancer cells can thus be displayed.

In the field of vessel examination OCT is used, as is described for example in WO 97/32182 A1, to generate images from the insides of the vessels using image-producing intravascular catheters. OCT is particularly suitable for example for qualitative plaque assessment. For this purpose OCT systems operate in a light wave range of approx. 1,300 nm. The light is emitted into the vessel wall from a catheter introduced into a vessel and the reflection from the vessel wall is registered in a depth-resolved manner, as described above, by means of interferometry. By translating the irradiated light beam information from various adjacent locations in the vessel wall can be obtained and compiled into a 2D image. The catheter can also be moved in the longitudinal axis of the vessel during image acquisition in order to sequentially display portions of the vessel that are located one behind the other.

The reflections of the various vessel wall layers carry the relevant image information and must be detected and displayed by the OCT device. The catheter itself has an internal structure which produces reflections, so the OCT system displays the catheter used in the image. OCT and the interferometry used for this purpose involve minimal differences in length which have to be detected. As, during catheter production, the manufacturing tolerances of the catheter length far exceed the differences in length that are to be measured, the OCT system must be re-calibrated for each new OCT catheter which is used as disposable material.

It is known here to make use of the autoreflections from the catheter itself. As the manufacturing tolerance of the diameter of the OCT catheter, which is visible in the center of the OCT image, is negligible compared with the differences in length that are to be measured, markings are usually displayed on the screen of the OCT system for calibration purposes, the spacing of which markings from each other corresponds to the known diameter of the OCT catheter. During calibration the user manually adjusts the length of the measuring path until the marking and the displayed reflection of the catheter match.

If the OCT catheter is advanced or withdrawn the optical fiber, which is part of the measuring path, in the catheter is compressed or elongated by a few micrometers. The changed length of the OCT catheter, or its core, changes the calibration, so length measurements in photographs which are caused by a movement of the catheter contain substantial errors and thus cannot be utilized for the examination. Manual recalibration is not possible as the catheter moves very quickly.

SUMMARY OF THE INVENTION

The object of the invention is therefore to develop a method which continuously recalibrates photographs which are produced during a longitudinal movement of the OCT catheter.

This object is achieved by the features of the independent claims. Advantageous developments of the invention are the subject of the subordinate claims.

The inventors recognized that it is automatically possible to directly influence both the change in the length of the optical fiber in a moved catheter as well as indirectly correct the effect of such changes in length in the generated image if, with the aid of image analysis, an object which is known in its dimension is continuously registered in the scanning region of the OCT catheter and the displayed dimension thereof is compared with the known actual dimension and is re-corrected according to a detected change in dimension. The correction measure can for example be a purely electronically executed change in the scale of the display of a scanned image, or one of the light paths of the measuring or reference beam can also be directly corrected in terms of its length. The delay time of the light through the measuring or reference path may also be influenced, and this also corresponds to a change in the length of the light path. A combination of a plurality of variants is also possible, in particular if the developments of the individual variants have different reaction times and adjustment speeds. Thus it may for example be advantageous to firstly electronically compensate, in the image itself, a change in the scale of the image display as soon as this is detected and to subsequently make a change in the mechanical length of a light path.

According to this basic idea the inventors propose improving the method, known per se, for tomographically displaying a cavity, preferably a blood vessel, by Optical Coherence Tomography (OCT), wherein, as is known, a scanning head with a catheter is introduced into the cavity to be optically scanned and the surroundings of the scanning head are shown in a tomographical display on the basis of detected interferences and their intensities between a measuring light beam and a reference light beam, wherein the path length of the measuring light beam in the catheter can change as a result of a movement of the catheter and brings about a change in the display scale. The improvement lies in the fact that a possible change in the path length of the measuring light beam in the event of a movement of the catheter is electronically determined and automatically compensated.

For this purpose there is the possibility of directly determining the change in the length of the measuring path interferometrically, preferably with the aid of an additional interferometer, and using it for calibration.

Alternatively, an object that is known by its dimension can also be scanned by the measuring light beam, be detected and measured in the tomographical display of this object by a continuous image analysis, and a correction can automatically be made with the aid of the detected dimension of the known object.

As a result of this continuous and automatic length tracking or calibration of the display, it is accordingly possible to maintain the display of the tomographic image such that it can be interpreted and utilized even during longitudinal movements of the catheter, for example during what is known as a pullback. It is therefore accordingly possible for the operator to assess the characteristic of a blood vessel with movement of the catheter much more easily.

In a particular embodiment a change in the length of the path of the measuring light beam and/or reference light beam is made as the correction. It is also possible, in addition or alternatively, to change the delay time of the reference light beam and/or measuring light beam, more precisely of the wave packet transported there, for the correction.

A further correction possibility consists in changing the scale of the display.

The catheter diameter in the region of the scanning head can preferably be used as the object whose dimensions are known for the above-mentioned measures. This can be seen in the display of the scan anyway and its diameter is known with a high degree of accuracy. On the other hand, an additional reference object in the scanning region of the scanning head can also be introduced and used for calibration as the object whose dimensions are known.

Such an object with a known dimension, preferably the diameter of the catheter located in the center of the image, can for example be determined by edge detection, so simple continuous calibration can be carried out.

In addition there is the possibility of directly determining the change in length or lengths of the measuring path by way of an interferometric measurement and of using these measured values for continuous calibration.

According to the above-described method, the inventors also propose the improvement in an OCT (=Optical Coherence Tomography) device for tomographically displaying an examined object, which contains:

a coherent laser light source,
a splitter for splitting the light emitted by the laser light source,
a length-adjustable reference light path into which the laser light source irradiates with a first portion of the emitted light (=reference light beam),
a length-adjustable measuring light path, at least partially extending in a catheter, into which the laser light source irradiates with a second portion of the emitted light (=measuring beam), comprising an optical scanning head which radially scans its surroundings at least in one plane,
an interference detector with an input for the reference light path and the measuring light path, and
a computing and display device for tomographically displaying the surroundings of the scanning head on the basis of the detected interference intensity between measuring beam and reference beam, wherein a part of the OCT device, preferably a catheter end, is visible in the tomographical display.

The improvement according to the invention in the OCT device lies in the fact that the computing and display device contains a program code which during operation executes the steps of the method described above.

BRIEF DESCRIPTION OF THE DRAWINGS

The invention will be described in more detail hereinafter with reference to a preferred embodiment and using the figures, wherein only the features required for an understanding of the invention are illustrated. The following reference characters will be used: 1: computing unit; 2: OCT device; 3: laser; 4: semi-transparent mirror; 5: mirror; 6: catheter; 7: scanning head; 8: blood vessel; 9: cutting plane; 10: interferometer/detector; 11: reference path; 12: measuring path; 13: outer edge of the catheter in the region of the scanning head/ring; 14: second interferometer; 15: second semi-transparent mirror; 16: common light path; 17: mirror; d: diameter of the catheter in the region of the scanning head; $Prg_1$-$Prg_n$: program for graphical display, evaluation of the tomographical display and calibration.

In the figures.

DETAILED DESCRIPTION OF THE INVENTION

Figure 1:
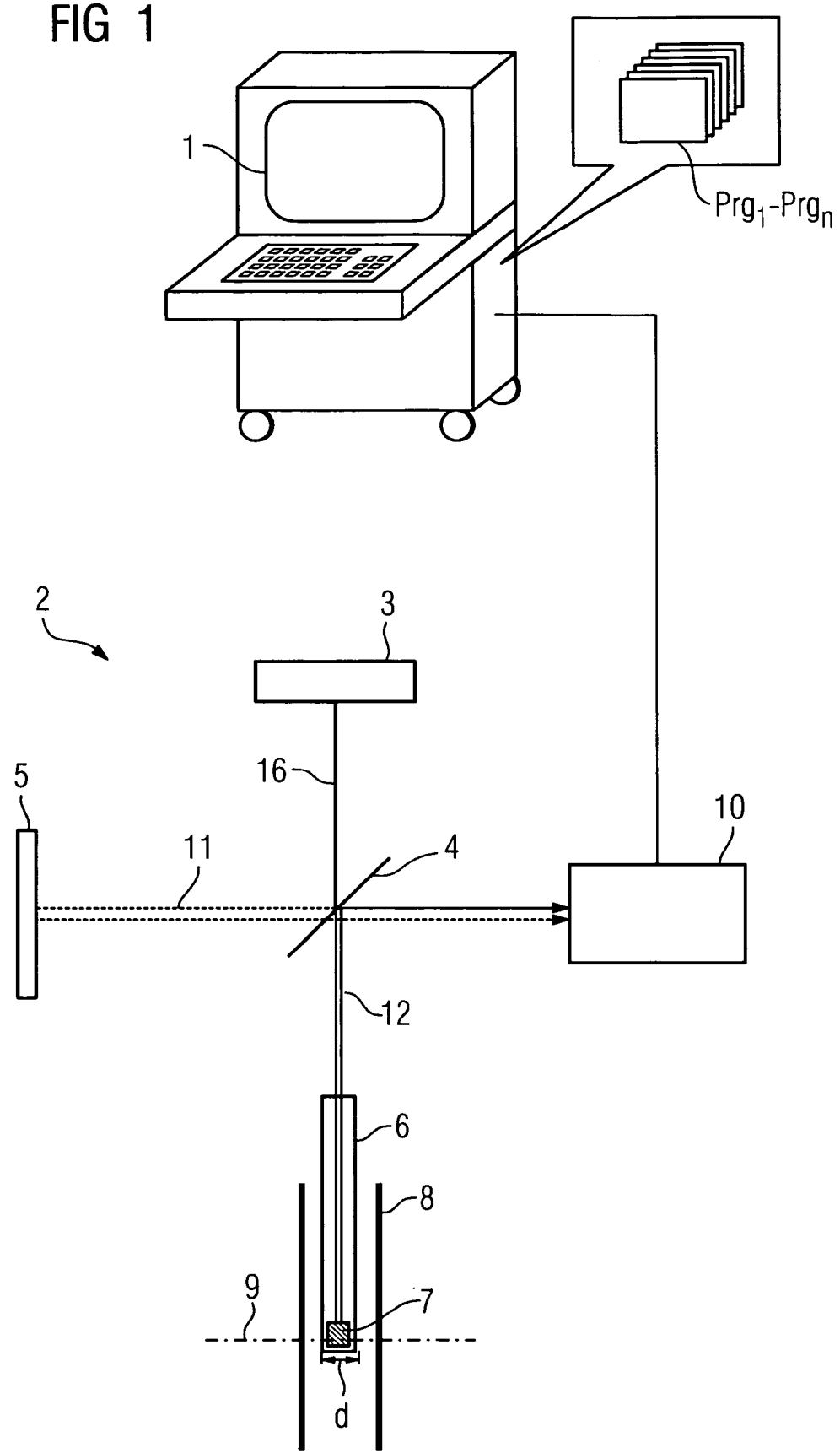
FIG. 1 shows a schematic diagram of an OCT device.

FIG. 1 shows an OCT device known per se with a computing unit 1 and the actual OCT unit 2. This is constructed from a laser 3 which, via a common light path 16, emits coherent light radiation to a semi-transparent mirror 4. At this semi-transparent mirror 4 a portion of the light is guided on the measuring path 12 to the scanning head 7 of the catheter 6 where the surroundings of the blood vessel 8 (schematically shown here) are scanned in a plane 9. The reflected light is then returned to the measuring path 12 and reflected at the semi-transparent mirror to the subsequent detector 10. At the same time, a decoupled portion of the light is conveyed to the reference path 11 at the semi-transparent mirror 4. A mirror 5, which conveys the light back and through the semi-transparent mirror 4 to the detector 10, is located in this reference path 11.

The two overlapping light beams are detected in the detector in the region of the scanning head 7 with respect to their interference intensity as a function of a variation in the length of the reference path and the respective angle of the emitted light, so, following an evaluation in the computing unit 1, a tomographic image of the surroundings of the scanning head 7 can be created.

Figure 2:
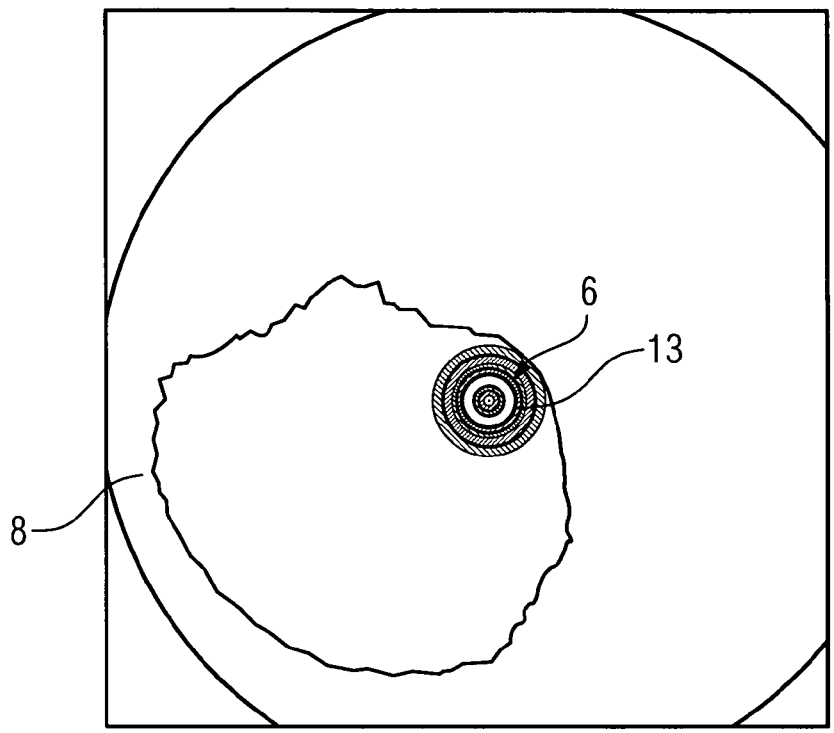
FIG. 2 tomographically shows a blood vessel with catheter.

FIG. 2 shows an exemplary tomographical photograph of this type in the plane 9 of a blood vessel 8 in which a catheter 6 is located, wherein the outer edge of the catheter 6 is reproduced by the concentric circle 13.

Figure 3:
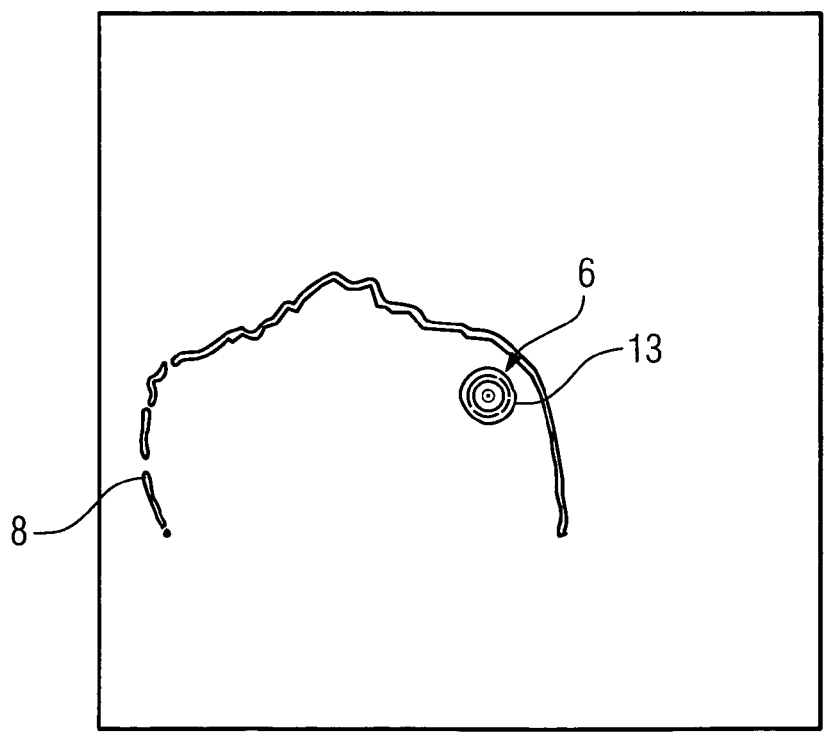
FIG. 3 shows photographs from FIG. 2 but with extracted edges.

FIG. 3 situated below shows the same photograph but with the edges electronically emphasized, so simple detection of this diameter d of the catheter can be determined in the region of the scanning head 7. The illustrated tomographic image of the blood vessel 8 may be calibrated using this displayed diameter d. According to the invention calibration takes place electronically and continuously during the examination, so the display can be utilized even in the event of movements of the catheter 6 in the blood vessel 8.

Figure 4:
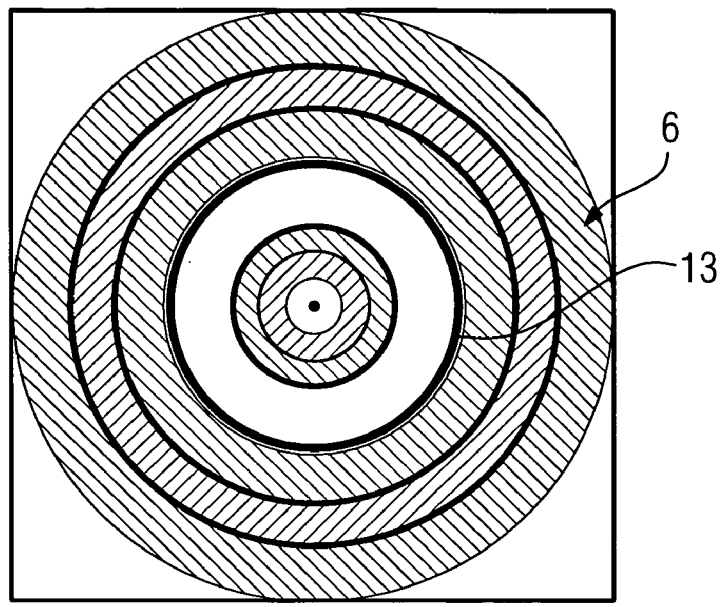
FIG. 4 shows an enlargement of a detail around the catheter from the photograph in FIG. 2.
Figure 5:
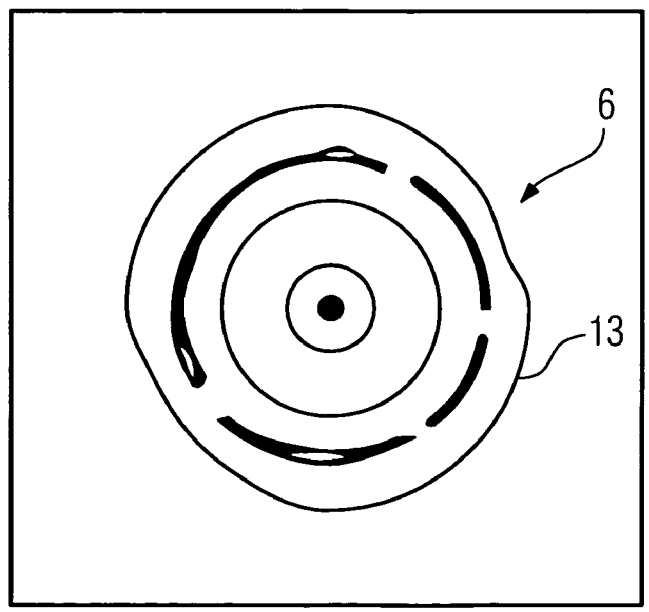
FIG. 5 shows an enlargement of a detail around the catheter from the photograph in FIG. 3.

For clarification FIGS. 4 and 5 again show enlargements of details from the center of the diagrams of FIGS. 2 and 3, in which the surrounding area of the catheter 6 is shown with its diameter d.

Thus the catheter edge, which is shown as an emphasized ring 13 with diameter d, can be tracked in the images in order to obtain information about the compression or elongation of the display via the change in the radius of the ring. Alternatively other signals visible in the image may also be tracked. However the catheter ring 13 is expedient as the potential search space is much smaller than the entire image as the center of the ring is also always disposed in the center of the image and therefore the detail of the image to be scanned is known. This considerably simplifies automatic object finding.

Tracking of the ring 13 proves to be much simpler here than the "free" finding of any desired object in an image, primarily because both the previous position of the ring and the direction of movement are known. Thus when the catheter is advanced the ring becomes smaller and when the catheter is withdrawn the ring becomes larger. Algorithms for tracking the ring are generally known.

If the ring is found in the image its radius can be determined and thus the change in the calibration. This information is accordingly used to recalibrate adaptively, either in terms of hardware, for example by mechanical adjustment of the light run length of the catheter, or in terms of software, by way of a radial elongation or compression of the image.

In general the information about the change can be used to control the calibration device in the system and thus make the correction. In principle the correction may also be made via additional mechanisms. The length of the optical fibers can be changed, for example by additional opposing elongation/relaxation of the fibers or by insertion of an optical delay. An adjustment of the reference run length may also be made on the hardware side, for example by additional displacement of the reference mirror. A further possibility of calibration is radial correction of the image itself. In this case the pixels are either inwardly or outwardly displaced along the radius by a fixed offset, which corresponds to the elongation/compression of the catheter.

However there is a limitation to this method if, in the case of an advance, the compression of the catheter is larger than the radius of the ring to be tracked. The ring can possibly disappear in this case and thus no longer be tracked. Precise calibration is no longer possible. However the actual catheter movement is the "pullback", in other words the controlled withdrawal of the catheter, in which the ring becomes ever larger. Tracking is thus not a problem in this case.

An alternative possibility of measuring the change in calibration consists in measuring signals not contained in the image and determining their change. A signal that is suitable for this purpose is for example the light which is reflected at the end of the optical fibers at the transition to the lens. In principle a portion of the light is reflected at each boundary that has a refractive index gradient. The light reflected at this boundary contains the information about the current length of the optical fibers. One possibility consists in fitting an additional interferometer and integrating the measuring beam into the device. The interferometry technique for exact length measurement is generally known. In principle other measuring techniques which can detect a change in the length of the optical fibers can also be used.

Figure 6:
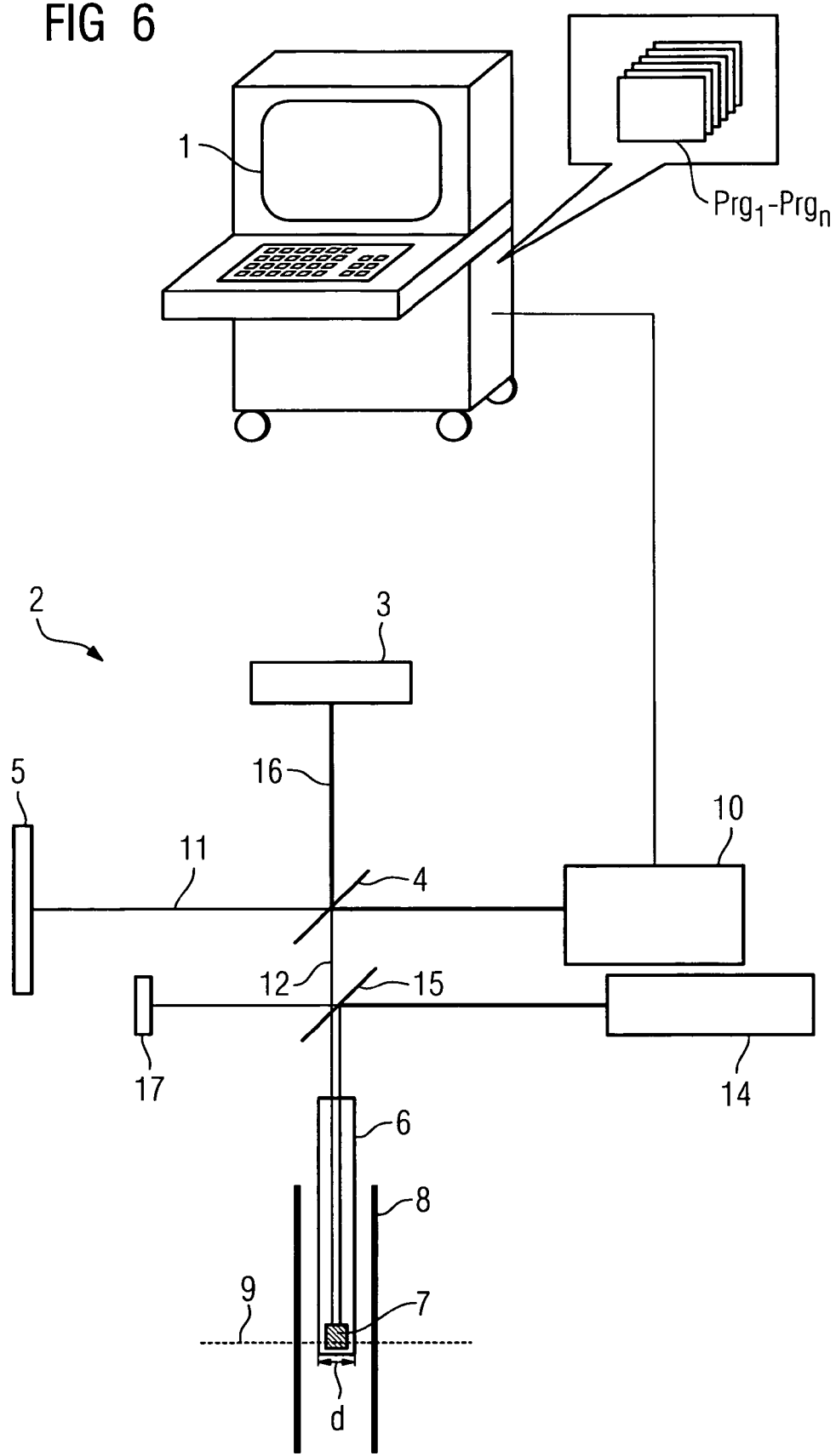
FIG. 6 shows a schematic diagram of an OCT device with additional interferometer for measuring the length of the measuring path.

FIG. 6 shows an OCT device of this type according to the OCT device shown in FIG. 1, although an additional interferometer 14, for directly determining the length of the measuring path, is integrated and carries out a direct length measurement of the measuring path via an additional semi-transparent mirror 15 and a further mirror 17.

It is understood that, in addition to the respectively disclosed combinations, the above-cited features of the invention can also be used in other combinations or alone without departing from the scope of the invention.

The invention claimed is:

1. A method for tomographically displaying a cavity by Optical Coherence Tomography (OCT), comprising:
    emitting light with a coherent laser light source;
    splitting the emitted light into a measuring light beam and a reference light beam;
    inserting a scanning head with a catheter which contains the measuring light beam into the cavity;
    scanning a surrounding of the cavity in a plane with the scanning head;
    tomographically displaying the surrounding of the cavity based on detected interferences and intensities between the measuring light beam and the reference light beam, wherein a length of the measuring light beam changes as a result of a movement of the catheter and brings a change in a display scale of the cavity;

determining the change in the length of the measuring light beam as the result of the movement of the catheter; and automatically compensating the change in the length of the measuring light beam as the result of the movement of the catheter, wherein the change in the length of the measuring light beam is directly determined via an additional interferometer used for calibration.

2. The method as claimed in claim 1, wherein an object whose dimensions are known is scanned by the measuring light beam, wherein a detection of dimensions of the object is carried out via a continuous image analysis, and wherein a correction is automatically made based on the detected dimensions of the object.

3. The method as claimed in claim 2, wherein a diameter of the catheter in a region of the scanning head is used as the object whose dimensions are known.

4. The method as claimed in claim 3, wherein the diameter of the catheter located in a center of an image is determined by edge detection and the image is continuously calibrated based on the diameter.

5. The method as claimed in claim 2, wherein an additional reference object in a scanning region of the scanning head is introduced and used for calibration as an object whose dimensions are known.

6. The method as claimed in claim 1, wherein a change in the length of the measuring light beam is corrected.

7. The method as claimed in claim 1, wherein a change in the length of the reference light beam is corrected.

8. The method as claimed in claim 1, wherein a delay time of the reference light beam is corrected.

9. The method as claimed in claim 1, wherein a delay time of the measuring light beam is corrected.

10. The method as claimed in claim 1, wherein a change of the display scale of the cavity is corrected.

11. An Optical Coherence Tomography (OCT) device for tomographically displaying an examined object, comprising:

a coherent laser light source for emitting light;

a splitter for splitting the light emitted by the coherent laser light source into a reference light beam and a measuring light beam;

a length-adjustable reference light path which contains the reference light beam;

a length-adjustable measuring light path partially extendable to a catheter which contains the measuring light beam, wherein the length-adjustable measuring light path comprises an optical scanning head which radially scans a surrounding of the examined object in a plane;

an interference detector for inputting the reference light beam and the measuring light beam;

a display device for tomographically displaying the surrounding of the examined object based on detected interferences and intensities between the measuring light beam and the reference light beam;

a computing device with a computer code for determining and compensating a change in a length of the measuring light beam as a result of a movement of the catheter; and an additional interferometer for direct detection of the length of the measuring light beam.

12. The OCT device as claimed in claim 11, wherein a part of the OCT device is tomographically visible in the display device.

13. The OCT device as claimed in claim 12, wherein the part of the OCT device which is tomographically visible in the display device is an end of the catheter.

\* \* \* \* \*